United States Patent [19]
Greenlee et al.

[11] Patent Number: 5,124,327
[45] Date of Patent: Jun. 23, 1992

[54] HIV REVERSE TRANSCRIPTASE

[75] Inventors: William J. Greenlee, Teaneck, N.J.; P. C. Srinivasan, Madras, India

[73] Assignee: Merck & Co., Inc., Rahway, N.J.

[21] Appl. No.: 755,922

[22] Filed: Sep. 6, 1991

[51] Int. Cl.$^5$ .................... A61K 31/40; A61K 31/535
[52] U.S. Cl. .................................. 514/235.2; 514/414; 514/418; 544/144; 548/484
[58] Field of Search .................. 514/235.2, 414, 418

[56] References Cited

U.S. PATENT DOCUMENTS 4,873,259 10/1989 Summers, Jr. et al. ............. 514/418

OTHER PUBLICATIONS

Lyle et al., *J. Med. Chem.*, vol. 34 (1991) pp. 1228–1230.

Primary Examiner—Robert W. Ramsuer
Attorney, Agent, or Firm—Roy D. Meredith; Charles M. Caruso; Carol S. Quagliato

[57] ABSTRACT

Novel indole compounds inhibit HIV reverse transcriptase, and are useful in the prevention or treatment of infection by HIV and the treatment of AIDS, either as compounds or pharmaceutical composition ingredients, whether or not in combination with other antivirals, anti-infectives, immunomodulators, antibiotics or vaccines. Methods of treating AIDS and methods of preventing or treating infection by HIV are also described.

1 Claim, No Drawings 5,124,327

HIV REVERSE TRANSCRIPTASE

The present invention is concerned with compounds which inhibit the reverse transcriptase encoded by human immunodeficiency virus (HIV) and are of value in the prevention of infection by HIV, the treatment of infection by HIV and the treatment of the resulting acquired immune deficiency syndrome (AIDS). It also relates to pharmaceutical compositions containing the compounds and to a method of use of the compounds and other agents for the treatment of AIDS and viral infection by HIV.

BACKGROUND OF THE INVENTION

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is reverse transcription of the RNA genome by a virally encoded reverse transcriptase to generate DNA copies of HIV sequences, a required step in viral replication. It is known that some compounds are reverse transcriptase inhibitors and are effective agents in the treatment of AIDS and similar diseases, e.g., azidothymidine or AZT.

Nucleotide sequencing of HIV shows the presence of a pol gene in one open reading frame [Ratner, L. et al., Nature, 313, 277(1985)]. Amino acid sequence homology provides evidence that the pol sequence encodes reverse transcriptase, an endonuclease and an HIV protease [Toh, H. et al., EMBO J. 4, 1267 (1985); Power, M. D. et al., Science, 231, 1567 (1986); Pearl, L. H. et al., Nature 329, 351 (1987)].

The compounds of this invention are inhibitors of HIV reverse transcriptase. Furthermore, the compounds of the present invention do not require bioactivation to be effective.

BRIEF DESCRIPTION OF THE INVENTION

Novel compounds of structural formula I

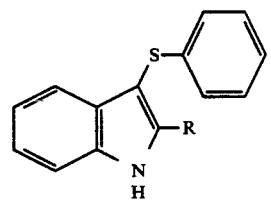

are disclosed. Compounds of formula I are useful in the inhibition of HIV reverse transcriptase, the prevention of infection by HIV, the treatment of infection by HIV and in the treatment of AIDS and/or ARC, either as compounds, pharmaceutical composition ingredients whether or not in combination with other antivirals, anti-infectives, immunomodulators, antibiotics or vaccines. Methods of treating AIDS, methods of preventing infection by HIV, and methods of treating infection by HIV are also disclosed.

DETAILED DESCRIPTION OF THE INVENTION AND PREFERRED EMBODIMENTS

This invention is concerned with the use of novel compounds of formula I in the inhibition of HIV reverse transcriptase, the prevention or treatment of infection by HIV and in the treatment of the resulting acquired immune deficiency syndrome (AIDS). The compounds of this invention are those with structural formula I:

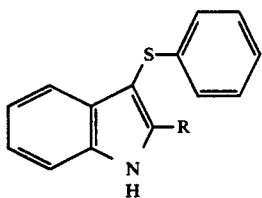

wherein R is

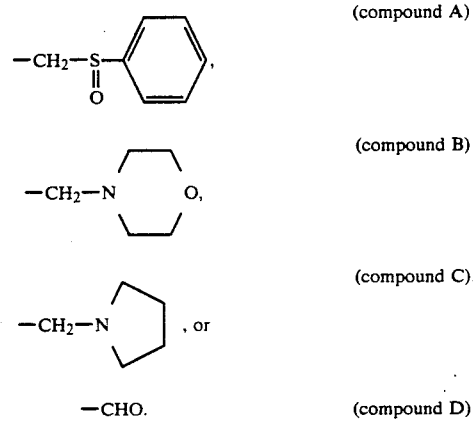

Compounds of formula I may have asymmetric centers and occur as racemates, racemic mixtures, or enantiomers with all isomeric forms being included in the present invention.

Abbreviations that may appear in this application are as follows:

| | |
|---|---|
| Me | methyl |
| Et | ethyl |
| Ph | phenyl |
| BuLi | butyllithium |
| n-Bu$_3$P | tri-n-butyl phosphine |
| LAH | lithium aluminum hydride |
| DMF | dimethylformamide |
| THF | tetrahydrofuran |
| Et$_3$N | tri-ethylamine |
| MMPP | monoperoxyphthalic acid, magnesium salt |
| BOP-reagent | benzotriazol-l-yloxytris-(dimethylamino)phosphonium hexaflurorphosphate |
| mp or m.p. | melting point |

Scheme I for preparing compound A is presented below.

SCHEME I

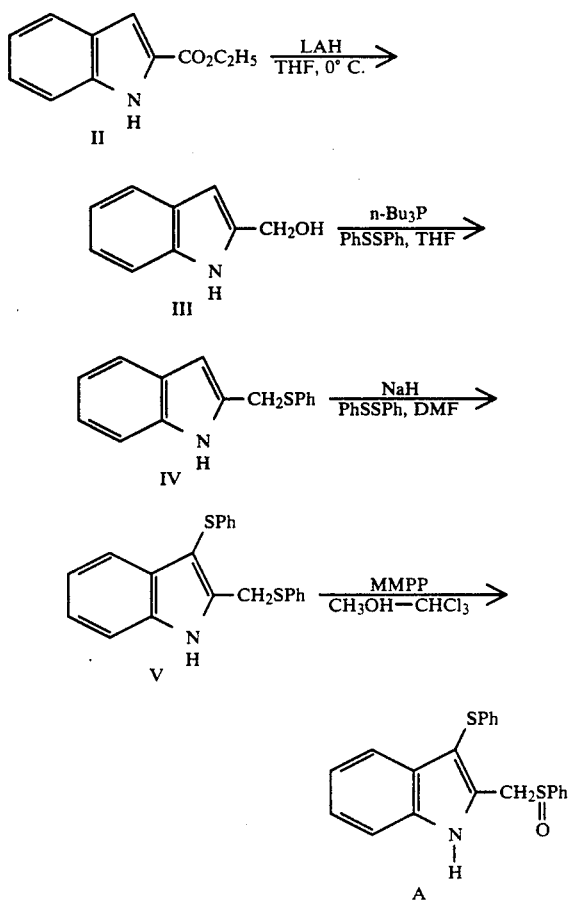

As shown in Scheme I, commercially available ethyl indole-2-carboxylate II is reduced to the primary alcohol III with an excess of lithium aluminum hydride in tetrahydrofuran at 0° C. Compound III is converted to the sulfide IV by treatment with an excess of tri-n-butylphosphine and phenyldisulfide in tetrahydrofuran at 0° C. to 20° C. for 6-24 hours. Reaction of sulfide IV with sodium hydride, and phenyldisulfide, in dimethylformamide at 0° C. to 20° C. for 1 to 18 hours produces bis-sulfide V. Thereafter, compound V is treated with one equivalent of peracid such as monoperoxyphthalic acid, magnesium salt (MMPP), or meta-chloroperoxybenzoic acid in methanol or chloroform-methanol at 0° C. for 30 minutes to 3 hours, to give predominately sulfoxide A.

The compounds of formula I are useful in the inhibition of HIV reverse transcriptase, the prevention or treatment of infection by the human immunodeficiency virus (HIV) and the treatment of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by, e.g., blood transfusion, organ transplant, exchange of body fluids, bites, accidental needle stick, or exposure to patient blood during surgery.

For these purposes, the compounds of the present invention may be administered orally, parenterally (including subcutaneous injections, intravenous, intramuscular, intrasternal injection or infusion techniques), by inhalation spray, or rectally, in dosage unit formulations containing conventional non-toxic pharmaceutically-acceptable carriers, adjuvants and vehicles.

Thus, in accordance with the present invention there is further provided a method of treating and a pharmaceutical composition for treating HIV infection and AIDS. The treatment involves administering to a patient in need of such treatment a pharmaceutical composition comprising a pharmaceutical carrier and a therapeutically-effective amount of a compound of the present invention.

The pharmaceutical composition may be in the form of orally-administrable suspensions or tablets; nasal sprays; sterile injectable preparations, for example, as sterile injectable aqueous or oleagenous suspensions or suppositories.

When administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweetners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these compositions may be prepared by mixing the drug with a suitable non-irritating excipient, such as cocoa butter, synthetic glyceride esters or polyethylene glycols, which are solid at ordinary temperatures, but liquidify and/or dissolve in the rectal cavity to release the drug.

The compounds of this invention can be administered orally to humans in a dosage range of 1 to 100 mg/kg body weight in divided doses. One preferred dosage range is 1 to 10 mg/kg body weight orally in divided doses. Another preferred dosage range is 1 to 20 mg/kg body weight orally in divided doses. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The present invention is also directed to combinations of the HIV reverse transcriptase inhibitor compounds with one or more agents useful in the treatment of AIDS. For example, the compounds of this invention may be effectively administered, whether at periods of pre-exposure and/or post-exposure, in combination with effective amounts of the AIDS antivirals, immunomodulators, anti-infectives, or vaccines known to those of ordinary skill in the art.

It will be understood that the scope of combinations of compounds of formula I with AIDS antivirals, immunomodulators, anti-infectives or vaccines include in principle any combination with any pharmaceutical composition useful for the treatment of AIDS.

REVERSE TRANSCRIPTASE ASSAY

The assay measures the incorporation of tritiated deoxyguanosine monophosphate by recombinant HIV reverse transcriptase (HIV $RT_R$) (or other RT) into acid-precipitable cDNA at the Km values of dGTP and poly r(C).oligo d(G)$_{12-18}$. In this assay, compound A inhibits this incorporation.

Thirty uL of a reaction mixture containing equal volumes of: 500 mM Tris.HCl (pH 8.2), 300 mM MgCl$_2$, 1200 mM KCl, 10 mM DTT, 400 µg/mL poly r(c).oligo d(G) [prepared by dissolving 1.5 mg (25 U) poly r(C).oligo d(G) in 1.5 ml sterile distilled H$_2$O and diluting to 400 µg/ml], 0.1 µCi/µl [$^3$H] dGTP, 160 µM dGTP, was added to 10 µl sterile distilled H$_2$O, 2.5 µl of potential inhibitor and 10 µL of 5 nM purified HIV $RT_R$ in tubes. The mixture was incubated at 37° C. for 45 minutes.

After incubation is complete, the tubes were cooled in ice for 5 minutes. Ice-cold 13% TCA containing 10 mM NaPP$_i$ (200 µl) are added and the mixture incubated on ice for 30 minutes. The precipitated cDNA is removed by filtration using presoaked glass filters [TCA, NaPP$_i$]. The precipitate is then washed with 1N HCl, 10 mM NaPP$_i$. The filter discs are then counted in a scintillation counter.

Under these conditions [dGTP] and poly r(C).oligo d(G)$_{12-18}$ each are approximately equal to the appropriate Km value. Approximately 5-6,000 cpm of [$^3$H] GMP are incorporated into acid-precipitable material. The RT reaction is concentration- and time-dependent. DMSO (up to 5%) does not affect enzyme activity. The calculated IC$_{50}$ value for compound A is about 60 nM as tested in the above described assay.

INHIBITION OF VIRUS SPREAD

A. Preparation of HIV-infected MT-4 Cell Suspension.

MT cells were infected at Day O at a concentration of 250,000 per ml with a 1:2000 dilution of HIV-1 strain IIIb stock (final 125 pg p24/ml; sufficient to yield ≦1% infected cells on day 1 and 25-100% on day 4). Cells were infected and grown in the following medium: RPMI 1640 (Whittaker BioProducts), 10% inactivated fetal bovine serum, 4 mM glutamine (Gibco Labs) and 1:100 Penicillin-Streptomycin (Gibco Labs).

The mixture was incubated overnight at 37° C. in 5% CO$_2$ atmosphere.

B. Treatment with Inhibitors

Serial two-fold dilutions of compound were prepared in cell culture medium. At Day 1, aliquots of 125 µl of compound were added to equal volumes of HIV-infected MT-4 cells (50,000 per well) in a 96-well microtiter cell culture plate. Incubation was continued for 3 days at 37° C. in 5% CO$_2$ atmosphere.

C. Measurement of Virus Spread

Using a multichannel pipettor, the settled cells were resuspended and a 125 µl harvested into a separate microtiter plate. After the settling of the cells, the plates were frozen for subsequent assay of the supernatant for HIV p24 antigen.

The concentration of HIV p24 antigen was measured by an enzyme immunoassay, described as follows. Aliquots of p24 antigen to be measured were added to microwells coated with a monoclonal antibody specific for HIV core antigen. The microwells were washed at this point, and at other appropriate steps that follow. Biotinylated HIV-specific antibody was then added, followed by conjugated streptavidin-horseradish peroxidase. A color reaction occurs from the added hydrogen peroxide and tetramethylbenzidine substrate. Color intensity is proportional to the concentration of HIV p24 antigen.

The cell culture inhibitory concentration (CIC$_{95}$) for each compound is defined as that concentration which inhibited by greater than 95% the spread of infection, as assessed by a greater than 95% reduction in p24 antigen production relative to untreated controls. Compound A was found to have a CIC$_{95}$ value of about 100 nM in this assay.

EXAMPLE 1

Preparation of 2-Phenylsulfinylmethyl-3-phenylthioindole (compound A)

Step A: 2-Hydroxymethylindole

A suspension of lithium aluminum hydride (2.0 g, 0.20 mol) in tetrahydrofuran (100 mL) was cooled with stirring to 0° C. under nitrogen. A solution of ethyl indole-2-carboxylate (10.0 g, 0.052 mol) in tetrahydrofuran was added dropwise, maintaining the reaction temperature between 0°-5° C. After 1 h, the reaction was quenched with saturated sodium potassium tartrate solution. The reaction was filtered and the filter cake washed well with tetrahydrofuran. The tetrahydrofuran was evaporated in vacuo and the residue partitioned between ethyl acetate and water. The ethyl acetate solution was washed with water, saturated brine, dried over magnesium sulfate, filtered and freed of solvent. The title compound was obtained as a yellowish solid. NMR (CDCl$_3$): δ8.18 (1H, bs), 7.57 (1H, d, J=8 Hz), 7.35 (1H, d, J=8 Hz), 7.26 (1H, s), 7.18 (1H, dt, J=1, 8 Hz), 7.10 (1H, dt, J=1, 8 Hz), 6.41 (1H, bs), 4.84 (2H, s).

Step B: 2-Phenylthiomethylindole

2-Hydroxymethylindole (6.94 g, 0.047 mol) and phenyldisulfide (10.8 g, 0.049 mol) were dissolved in tetrahydrofuran (200 mL) and cooled to 0° C. under nitrogen. Tri-n-butylphosphine (11.7 mL, 0.047 mol) was added and the reaction stirred for 1 h. Additional phenyldisulfide (1.5 g, 0.007) and tri-n-butylphosphine (5.1 mL, 0.20 mol) was added, and the reaction stirred at room temperature until complete. The tetrahydrofuran was removed in vacuo and the residue chromatographed on silica gel eluting with 5% ethyl acetate in hexane. The title compound was obtained as clear colorless plates, mp 100°-101.5° C. Anal. Calc. for $C_{15}H_{13}NS$: C, 75.27, H, 5.47, N, 5.85. Found: C, 74.52, H, 5.39, N, 5.95.

Step C: 3-Phenylthio-2-phenylthiomethylindole

A suspension of sodium hydride (0.37 g 60% dispersion in oil, 9.4 mmol) in dimethylformamide (50 mL) was cooled to 0° C. 2-Phenylthiomethylindole (1.5 g, 6.3 mmol) was added portionwise, and the reaction stirred at 0° C. for 15 min. Phenyldisulfide (1.5 g, 6.9 mmol) was added and the reaction stirred at 20° C. for 6 h. The reaction was quenched with water and extracted with ethyl acetate. The organic extract was washed with water, saturated brine and dried over magnesium sulfate. Filtration and evaporation of solvent left an oil which was purified by medium pressure chromatography on silica gel using 5% ethyl acetate in hexane. The title compound was obtained as an oil. Anal. Calc. for $C_{21}H_{17}NS_2 \cdot H_2O \cdot 0.15\ C_4H_8O_2$: C, 68.50; H, 5.33; N 3.60. Found: C, 68.40; H, 4.65; N, 3.86.

Step D: 2-Phenylsulfinylmethyl-3-phenylthioindole

A solution of 3-phenylthio-2-phenylthiomethylindole (0.750 g, 2.94 mmol) in methanol (100 mL) was cooled to 0° C. with stirring. Monoperoxyphthalic acid magnesium salt (0.908 g 80% peracid) in methanol (50 mL) was added slowly dropwise. After addition, the reaction was stirred an additional 30 min., then quenched with 10% aqueous sodium thiosulfate (2 mL). The methanol was removed in vacuo, and the residue partitioned between ethyl acetate and water. The organic phase was washed successively with water and saturated brine, then dried over magnesium sulfate. Filtration and concentration of the filtrate in vacuo gave an oil which was purified by chromatography on silica gel using 20-30% ethyl acetate in hexane. The title compound was obtained as a foam, mp 71°-74° C. Exact mass calculated for $C_{21}H_{17}NOS_2$: 364.082982. Found: 364.084549. NMR (DMSO-$d_6$) $\delta$11.82 (1H, s), 7.50 (6H, m), 7.23 (1H, d, J=8 Hz), 7.15 (3H, m) 7.05 (2H, m) 6.90 2H, m), 4.43 (1H, d, J=13 Hz), 4.38 (1H, d, J=13 Hz).

EXAMPLE 2

Preparation of 2-morpholinomethyl-3-phenylthioindole (compound B)

Morpholine (0.220 mL, 2.5 mmol) is added to a solution of 3-phenylthioindole-2-carboxaldehyde (0.298 g, 1.0 mmol) in methanol at 20° C. Methanolic hydrochloric acid is added until the solution is pH 5. Sodium cyanoborohydride (0.63 g, 10.0 mmol) is added and the reaction stirred overnight. The reaction is diluted with water and extracted with ethyl acetate. The ethyl acetate solution is washed with water, saturated sodium chloride, and dried over magnesium sulfate. Filtration and concentrated in vacuo give the title compound which is purified by standard techniques well known in the art to those of ordinary skill, such as silica gel chromatography.

EXAMPLE 3

Preparation of 3-Phenylthio-2-pyrrolidinomethylindole (compound C)

3-Phenylthio-2-pyrrolidinomethylindole is prepared using substantially the same procedure as employed in Example 2, except substituting pyrrolidine for morpholine.

EXAMPLE 4

Preparation of 3-Phenylthioindole-2-carboxaldehyde (compound D)

Step A: N-Methoxy-N-methyl-3-phenylthioindole-2-carboxamide

Benzotriazol-1-yloxytris(dimethylamino)phosphonium hexafluorophosphate (1.64 g, 3.7 mmol) was added to a solution of 3-phenylthioindole-2-carboxylic acid (1.0 g, 3.7 mmol), N,O-dimethylhydroxylamine hydrochloride (0.54 g, 5.5 mmol) and triethylamine (1.5 mL, 11 mmol) in degassed dimethylformamide. The reaction was stirred at room temperature overnight. The precipitated product was filtered and the filter cake washed well with water. The solid was triturated with 30% ethyl acetate in hexane, filtered and dried at 60° C. in vacuo for 72 hours.

Step B: 3-Phenylthioindole-2-carboxaldehyde

N-Methoxy-N-methyl-3-phenylthioindole-2-carboxamide (1.57 g, 5.26 mmol) was dissolved in tetrahydrofuran (150 mL) and cooled to 0° C. under nitrogen. A solution of lithium aluminum hydride in tetrahydrofuran (5.76 mL, 1M) was added slowly via syringe and the reaction stirred a total of 1.5 hours. Ethyl acetate (30 mL) was added, followed by saturated sodium potassium tartrate solution. The layers were separated and the organic phase washed with saturated brine and dried over magnesium sulfate. Filtration and evaporation of solvent gave the title compound as a yellow solid.

While the foregoing specification teaches the principles of the present invention, with examples provided for the purpose of illustration, it will be understood that the practice of the invention encompasses all of the usual variations, adaptations, and modifications, as come within the scope of the following claims and its equivalents.

What is claimed is:

1. A method of inhibiting HIV reverse transcriptase, comprising administering to a mammal an effective amount of a compound of the formula

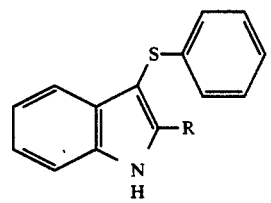

wherein R is

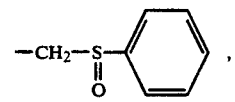,

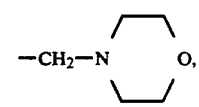,

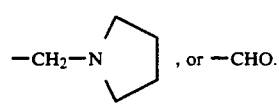

* * * * *